United States Patent
Murray et al.

(10) Patent No.: US 10,118,019 B2
(45) Date of Patent: Nov. 6, 2018

(54) CATHETER CARTRIDGE ASSEMBLIES AND METHODS OF USING THE SAME FOR INTERMITTENT CATHETERIZATION

(71) Applicant: Hollister Incorporated, Libertyville, IL (US)

(72) Inventors: Michael G. Murray, Ballina (IE); Patrick Enda O'Dowd, Dunsany (IE); Stephen Williams, Blackrock (IE)

(73) Assignee: Hollister Incorporated, Libertyville, IL (US)

( * ) Notice: Subject to any disclaimer, the term of this patent is extended or adjusted under 35 U.S.C. 154(b) by 264 days.

(21) Appl. No.: 15/105,267

(22) PCT Filed: Jan. 8, 2015

(86) PCT No.: PCT/US2015/010584
§ 371 (c)(1),
(2) Date: Jun. 16, 2016

(87) PCT Pub. No.: WO2015/105949
PCT Pub. Date: Jul. 16, 2015

(65) Prior Publication Data
US 2017/0000978 A1    Jan. 5, 2017

Related U.S. Application Data

(60) Provisional application No. 61/925,304, filed on Jan. 9, 2014.

(51) Int. Cl.
*A61M 25/01* (2006.01)
*A61M 25/00* (2006.01)
*A61M 25/16* (2006.01)

(52) U.S. Cl.
CPC ....... *A61M 25/0111* (2013.01); *A61M 25/002* (2013.01); *A61M 25/0017* (2013.01); *A61M 25/0136* (2013.01)

(58) Field of Classification Search
CPC ............ A61M 25/0017; A61M 25/002; A61M 25/0111; A61M 25/0136;
(Continued)

(56) References Cited

U.S. PATENT DOCUMENTS 3,053,257 A    9/1962    Blrtweli
3,154,080 A    10/1964   Rowan et al.
(Continued)

FOREIGN PATENT DOCUMENTS

WO    WO 9110466 A1    7/1991
WO    WO 9638192 A1    12/1996
(Continued)

OTHER PUBLICATIONS

Notification of Transmittal of the International Search Report and the Written Opinion of the International Searching Authority for PCT/US2015/010584, dated Mar. 27, 2015.

*Primary Examiner* — Adam Marcetich
(74) *Attorney, Agent, or Firm* — Cook Alex Ltd.

(57) ABSTRACT

A catheter cartridge assembly includes a cartridge and a catheter member. The cartridge has a cartridge housing with proximal and distal ends. A pre-loaded tip and a protective sleeve associated with the pre-loaded tip are at least partially positioned within the cartridge housing. The catheter member has a proximal end configured to be advanced proximally into and through the cartridge housing to engage a distal end of the pre-loaded tip for proximal advancement out of the proximal end of the cartridge housing with the pre-loaded tip, with the protective sleeve covering at least a portion of the catheter member.

19 Claims, 10 Drawing Sheets

(58) Field of Classification Search
CPC ...... A61M 2025/0024; A61M 25/0113; A61M 25/0119; A61M 5/3243; A61M 2025/0681; A61M 25/0026; A61M 2025/0175; A61M 2025/0034; A61M 2025/0063; A61M 25/0102; A61M 25/0194

See application file for complete search history.

(56) References Cited

U.S. PATENT DOCUMENTS

| | | | |
|---|---|---|---|
| 3,421,509 A | 1/1969 | Flore | |
| 3,894,540 A * | 7/1975 | Bonner, Jr. | A61M 25/0111 604/171 |
| 3,902,500 A | 9/1975 | Dryden | |
| 4,062,363 A | 12/1977 | Bonner, Jr. | |
| 4,327,723 A | 5/1982 | Frankhauser | |
| 4,327,735 A | 5/1982 | Hampson | |
| 4,515,592 A | 5/1985 | Frankhouser | |
| 4,634,433 A | 1/1987 | Osborne | |
| 4,652,259 A * | 3/1987 | O'Neil | A61M 25/0111 600/581 |
| 4,655,214 A | 4/1987 | Linder | |
| 4,767,409 A | 8/1988 | Brooks | |
| 4,955,858 A * | 9/1990 | Drews | A61F 2/04 600/434 |
| 5,098,379 A | 3/1992 | Conway et al. | |
| 5,209,726 A | 5/1993 | Goosen | |
| 5,234,411 A | 8/1993 | Vaillancourt | |
| 5,346,478 A | 9/1994 | Jinotti | |
| 5,417,666 A * | 5/1995 | Coulter | A61M 25/0111 604/172 |
| 5,749,357 A | 5/1998 | Linder | |
| 5,792,114 A * | 8/1998 | Fiore | A61M 25/0111 604/171 |
| 5,836,918 A * | 11/1998 | Dondlinger | A61M 1/008 604/171 |
| 5,906,575 A * | 5/1999 | Conway | A61F 2/0022 600/29 |
| 6,090,075 A | 7/2000 | House | |
| 6,217,569 B1 | 4/2001 | Fiore | |
| 6,471,684 B2 | 10/2002 | Dulak et al. | |
| 6,585,721 B2 | 7/2003 | Flore | |
| 6,610,035 B2 | 8/2003 | Yang et al. | |
| 7,311,698 B2 | 12/2007 | Tanghoj et al. | |
| 7,601,158 B2 | 10/2009 | House | |
| 7,662,146 B2 | 2/2010 | House | |
| 7,789,873 B2 | 9/2010 | Kubalak et al. | |
| 7,918,831 B2 | 4/2011 | House | |
| 7,922,712 B2 | 4/2011 | Tanghoj et al. | |
| 8,011,505 B2 | 9/2011 | Murray et al. | |
| 8,282,624 B2 | 10/2012 | Tanghoej et al. | |
| 2001/0007060 A1 * | 7/2001 | Fiore | A61M 25/0017 604/171 |
| 2001/0052658 A1 * | 12/2001 | Conway | A61F 2/0022 264/255 |
| 2005/0109648 A1 | 5/2005 | Kerzman et al. | |
| 2005/0197627 A1 * | 9/2005 | Huang | A61M 25/00 604/171 |
| 2006/0173467 A1 * | 8/2006 | Karwoski | A61F 2/06 606/108 |
| 2007/0088330 A1 | 4/2007 | House | |
| 2007/0225649 A1 | 9/2007 | House | |
| 2008/0015527 A1 | 1/2008 | House | |
| 2008/0091145 A1 | 4/2008 | House | |
| 2008/0097411 A1 | 4/2008 | House | |
| 2008/0147049 A1 | 6/2008 | House et al. | |
| 2008/0171998 A1 | 7/2008 | House | |
| 2008/0172042 A1 | 7/2008 | House | |
| 2009/0018530 A1 | 1/2009 | Nielsen et al. | |
| 2009/0036874 A1 | 2/2009 | Horowitz et al. | |
| 2010/0030197 A1 | 2/2010 | House | |
| 2010/0063513 A1 * | 3/2010 | Braga | A61B 17/32 606/108 |
| 2010/0145315 A1 | 6/2010 | House | |
| 2010/0198195 A1 | 8/2010 | Nishtala et al. | |
| 2010/0204682 A1 | 8/2010 | Tanghoj et al. | |
| 2011/0114520 A1 * | 5/2011 | Matthison-Hansen | A61M 25/002 206/364 |
| 2015/0320970 A1 * | 11/2015 | Foley | A61M 25/0111 604/544 |

FOREIGN PATENT DOCUMENTS

| | | |
|---|---|---|
| WO | WO 2005/014055 A2 | 2/2005 |
| WO | WO 2006 121508 A2 | 11/2006 |
| WO | WO 2013/130459 A1 | 9/2013 |

* cited by examiner

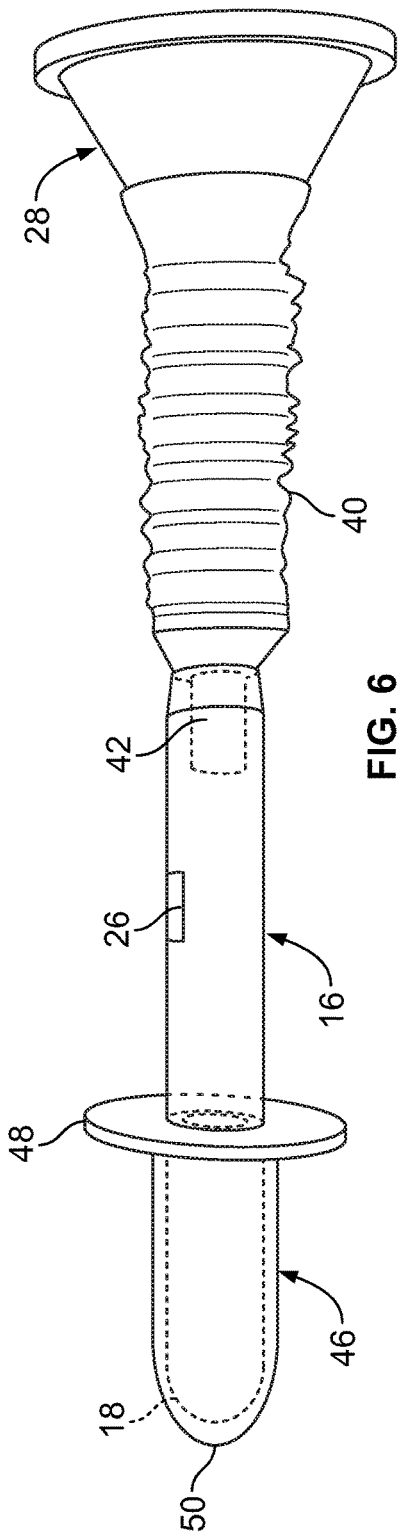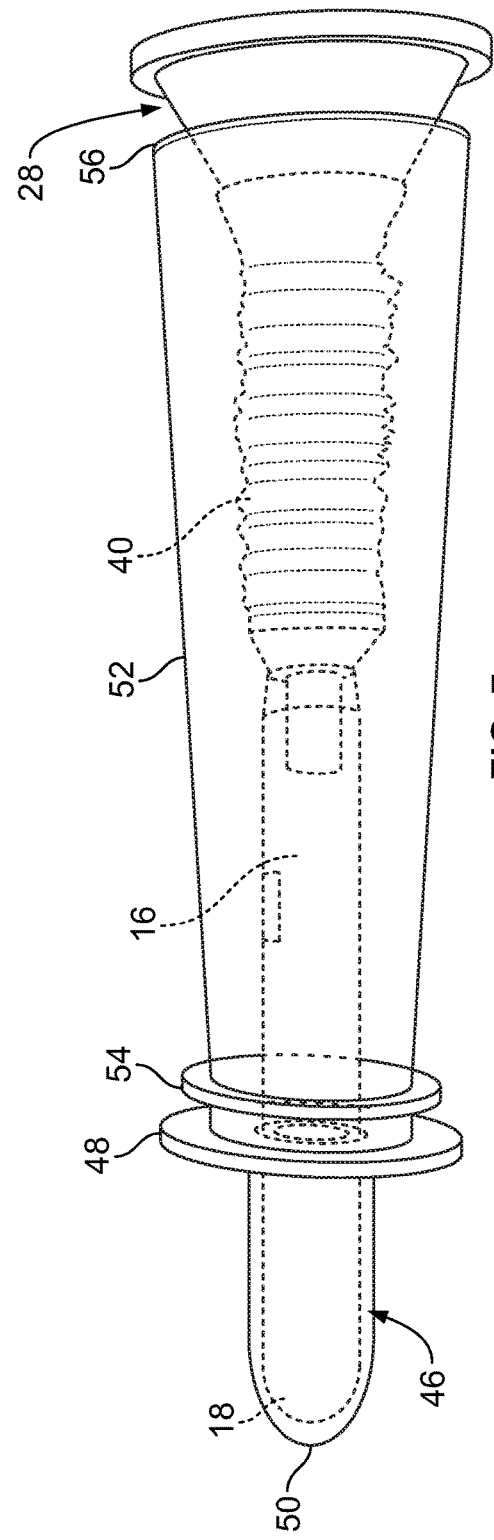

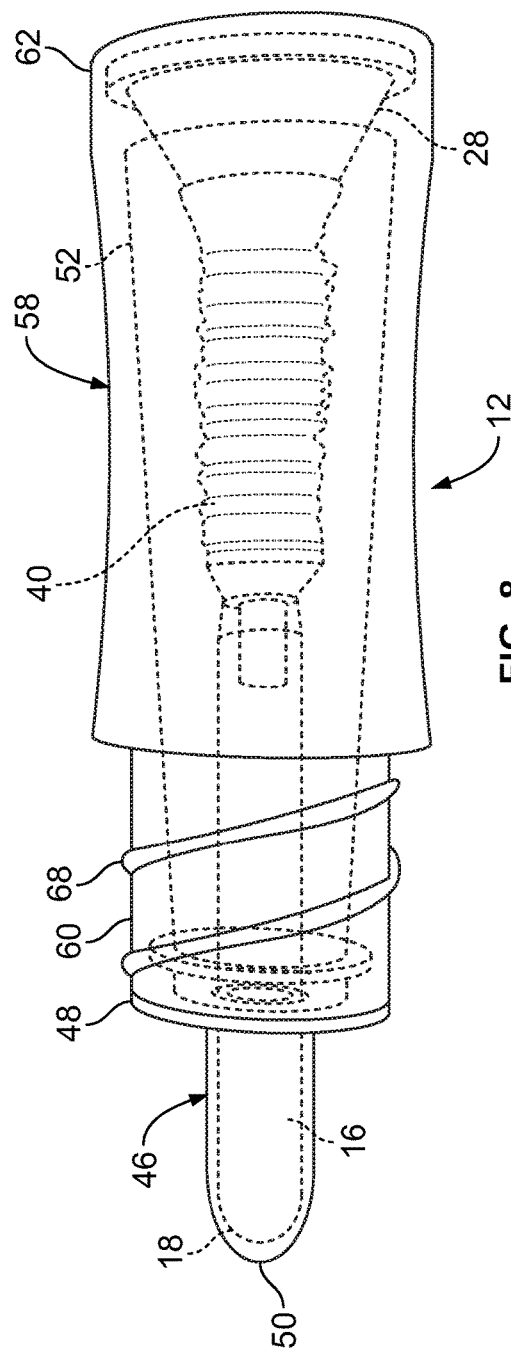
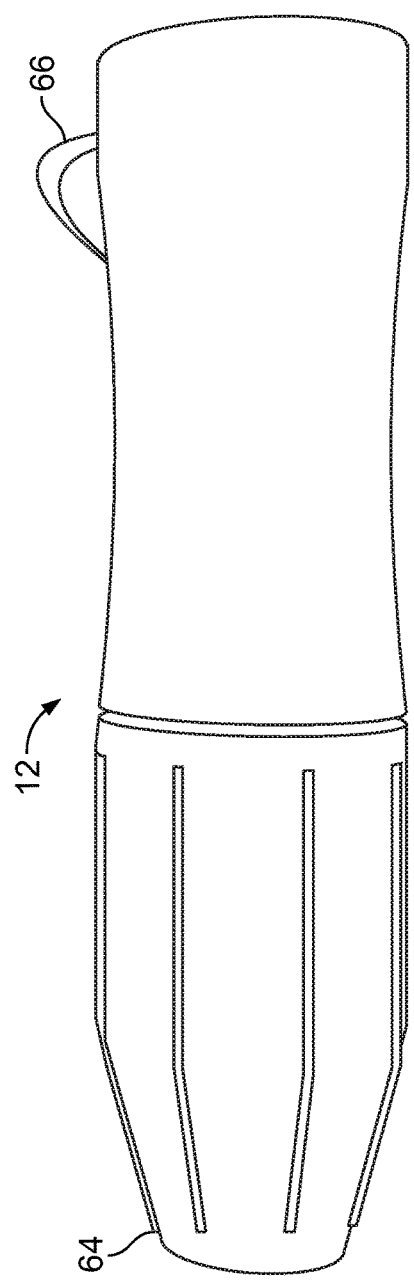
FIG. 8
FIG. 9

CATHETER CARTRIDGE ASSEMBLIES AND METHODS OF USING THE SAME FOR INTERMITTENT CATHETERIZATION

RELATED APPLICATION

This application is a U.S. national stage application of PCT Patent Application Serial No. PCT/US2015/010584, filed Jan 8, 2015, which claims the benefit of and priority of U.S. Provisional Patent Application Ser. No. 61/925,304, filed Jan. 9, 2014, the contents of both of which are incorporated by reference herein.

DESCRIPTION

Technical Field

The present disclosure generally relates to catheters. More particularly, the present disclosure relates to cartridges containing a lubricated sleeve for easing insertion of an intermittent catheter.

BACKGROUND

Catheters are used to treat many different types of medical conditions and typically include an elongated shaft that is inserted into and through a passageway or lumen of the body. Catheters, and in particular intermittent catheters, are commonly used by those who suffer from various abnormalities of the urinary system, such as urinary incontinence. With the advent of intermittent catheters, individuals with urinary system abnormalities can self-insert and self-remove intermittent catheters several times a day. Such catheters typically include a shaft that is sufficiently flexible to navigate the curves of the urethra (especially catheters intended for male users), yet rigid enough to be pushed through the urethra without collapsing or buckling before an end of the catheter reaches the bladder.

Known self-catheterization systems may have any of a number of disadvantages. For example, such systems may be large or otherwise inconvenient to transport multiples in one's pocket or on one's person or they may be difficult to use or dispose of after use. Accordingly, it would be advantageous to provide a self-catheterization system that overcomes these possible disadvantages of known systems.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a catheter cartridge assembly includes a cartridge and a catheter member. The cartridge has a cartridge housing with proximal and distal ends. A pre-loaded tip and a protective sleeve associated with the pre-loaded tip are at least partially positioned within the cartridge housing. The catheter member has a proximal end configured to be advanced proximally into and through the cartridge housing to engage a distal end of the pre-loaded tip for proximal advancement out of the proximal end of the cartridge housing with the pre-loaded tip. The protective sleeve covers at least a portion of the catheter member as it is proximally advanced out of the cartridge housing.

In another aspect, a catheterization method is provided for a cartridge of the type having a cartridge housing with proximal and distal ends. A pre-loaded tip and a protective sleeve associated with the pre-loaded tip are at least partially positioned within the cartridge housing. At least a proximal portion of a catheter member is proximally advanced into the cartridge housing via the distal end of the cartridge housing, with a proximal end of the catheter member engaging a distal end of the pre-loaded tip. So engaging the catheter member and the pre-loaded tip also has the effect of positioning at least the proximal portion of the catheter member within the protective sleeve. The pre-loaded tip and the proximal portion of the catheter member are advanced out of the cartridge housing via the proximal end of the cartridge housing, with the protective sleeve covering at least a portion of the catheter member.

BRIEF DESCRIPTION OF THE DRAWINGS

FIG. 6 is a side elevational view of the assembly of FIG. 5, with a portion of the pre-loaded tip positioned within an introducer;

FIG. 7 is a side elevational view of the assembly of FIG. 6, with portions of the pre-loaded tip and alignment member positioned within a lubrication reservoir;

FIG. 8 is a side elevational view of the assembly of FIG. 7, with the lubrication reservoir positioned within a cartridge housing;

FIG. 9 is a side elevational view of the assembly of FIG. 8, with a proximal enclosure associated with a proximal portion of the cartridge housing and a distal enclosure associated with a distal portion of the cartridge housing;

DETAILED DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Figure 1:
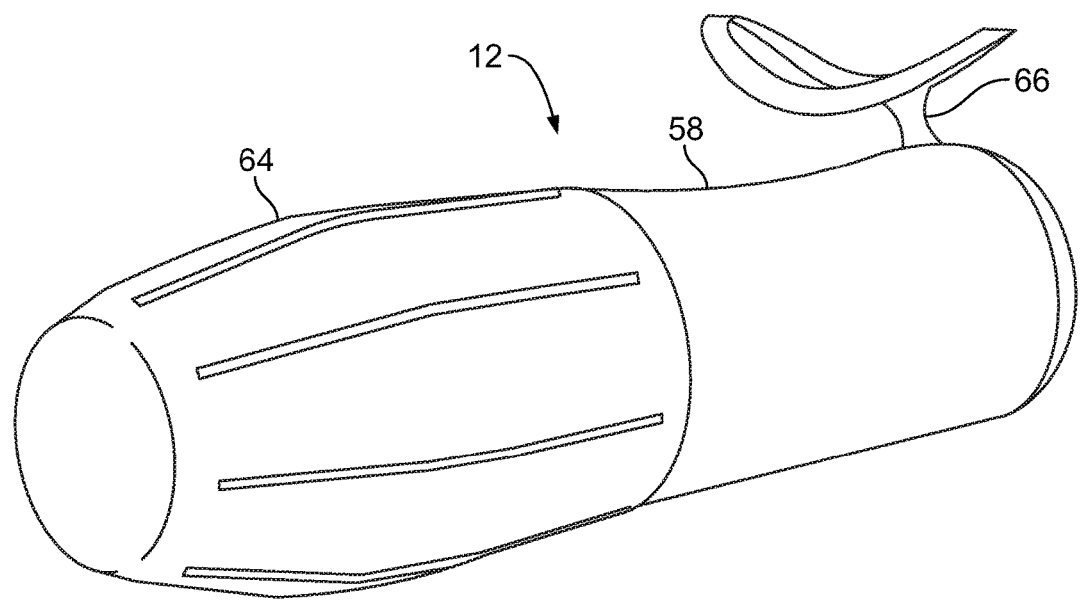
FIG. 1 is a perspective view of an embodiment of a cartridge of a catheter cartridge assembly according to an aspect of the present disclosure.
Figure 2:
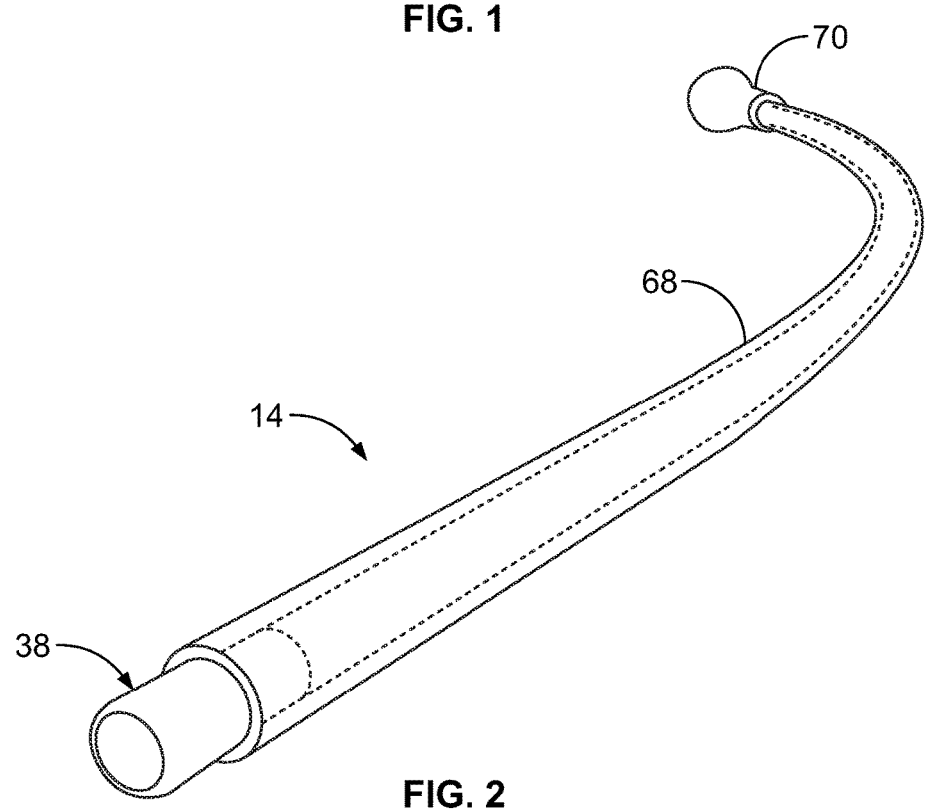
FIG. 2 is a perspective view of a catheter member of the catheter cartridge assembly, which may be used in combination with the cartridge of FIG. 1.

Catheter cartridge assemblies according to the present disclosure and their individual components may be variously configured without departing from the scope of the present disclosure, but in one embodiment, a catheter cartridge assembly 10 is provided as a kit, which includes a disposable cartridge 12 (FIG. 1) and a separate, reusable catheter member 14 (FIG. 2). The kit may include additional components (e.g., a fluid drainage bag or receptacle) without departing from the scope of the present disclosure. The illustrated cartridge 12 and catheter member 14 may have particular utility for intermittent catheterization of a male urethra (and will be described as such herein), but it is within the scope of the present disclosure for catheter cartridge assemblies of the type described herein to be used for intermittent catheterization of a female urethra or for use in any other appropriate body lumen.

Figure 3:
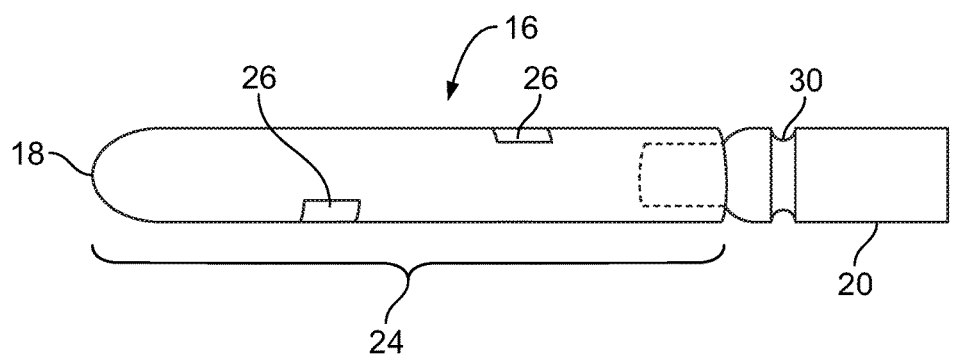
FIG. 3 is a side elevational view of a pre-loaded tip of the cartridge of FIG. 1.

The constituent components of the cartridge 12 of FIG. 1 are illustrated in greater detail in FIGS. 3-9. FIG. 3 shows a pre-loaded catheter tip 16 of the cartridge 12. The illustrated pre-loaded tip 16 extends between a proximal end 18 and a distal end 20. As will described herein, the pre-loaded tip 16 combines with the catheter member 14 to define a composite catheter 22 (FIG. 18), with the pre-loaded tip 16 providing the proximal insertion end of the composite catheter 22. Accordingly, at least a portion of the pre-loaded tip 16 (preferably a proximal portion 24) may be configured similarly to the proximal insertion end of a conventional catheter, such as a urinary catheter. In the illustrated embodiment, the proximal portion 24 of the pre-loaded tip 16 includes one or more side openings or eyes or drainage portions 26. The eyes 26 allow fluid (e.g., urine) to drain into and through the pre-loaded tip 16 to the distal end 20 of the pre-loaded tip 16, where it may flow into the associated catheter member 14, as will be described herein. The proximal end 18 of the pre-loaded tip 16 may be closed to ensure that fluid flowing into the pre-loaded tip 16 via the eyes 26 must flow toward and out of the distal end 20.

The distal end 20 of the pre-loaded tip 16 may be generally tubular or any other shape that is suitable to allow the distal end 20 to serve as a connector or fitting between the proximal portion 24 of the pre-loaded tip 16 and one or more other components of the catheter cartridge assembly 10. Accordingly, it may be advantageous for the distal end 20 to be formed of a material that is more rigid than the material used to form the proximal portion 24 of the pre-loaded tip 16, in which case the distal end 20 of the pre-loaded tip 16 may be separately manufactured from the proximal portion 24 before being secured thereto. Alternatively, it is also within the scope of the present disclosure for the distal end 20 to be integrally formed with the remainder of the pre-loaded tip 16.

Figure 4:
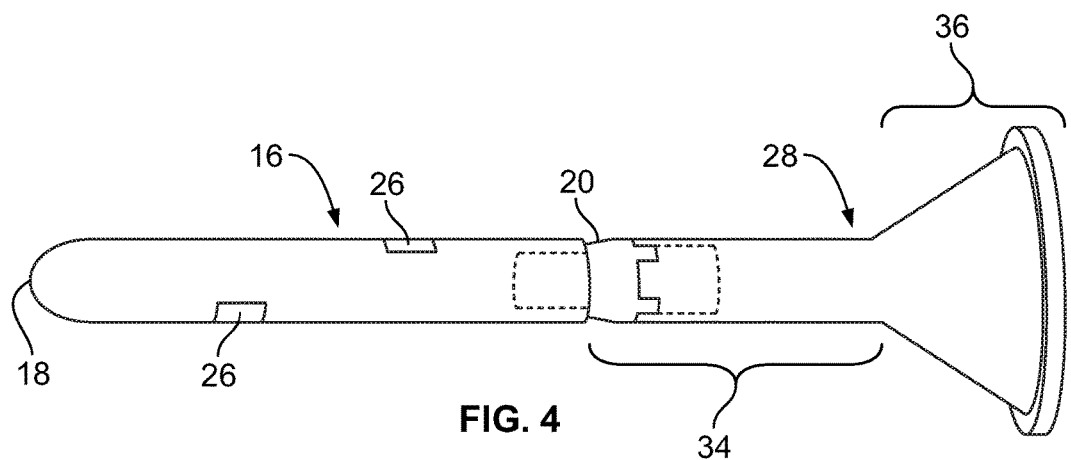
FIG. 4 is a side elevational view of the pre-loaded tip of FIG. 3, including an alignment member associated with a distal end thereof.

FIG. 4 shows the distal end 20 of the pre-loaded tip 16 serving as a connector to secure an optional alignment member 28 to the pre-loaded tip 16. In the illustrated embodiment, the external surface of the distal end 20 of the pre-loaded tip 16 includes a groove or formation 30 (FIG. 3) which receives a projection or ridge 32 of the alignment member 28 (FIG. 17) to retain the alignment member 28 on the pre-loaded tip 16. The illustrated arrangement provides a snap-fit between the pre-loaded tip 16 and the alignment member 28, which allows the pre-loaded tip 16 to be detached from the alignment member 28, as will be described in greater detail herein. While the illustrated embodiment provides a snap-fit between the pre-loaded tip 16 and the alignment member 28, other arrangements (e.g., a friction fit or press fit or interference fit or the like) may also be provided for detachably connecting the pre-loaded tip 16 and the alignment member 28.

The illustrated alignment member 28 includes a generally tubular proximal portion 34 and a generally non-tubular distal portion 36. As will be described in greater detail herein, the alignment member 28 (if provided) helps to guide the catheter member 14 into engagement with the pre-loaded tip 16, with the distal portion 36 preferably having a diameter that decreases from a distal end to a proximal end. By such a configuration, a catheter member 14 proximally advanced into the alignment member 28 (i.e., from right-to-left in the orientation of FIG. 4) will be directed into coaxial alignment with the central axis of the alignment member 28 and the pre-loaded tip 16 for engagement between a proximal end 38 of the catheter member 14 and the distal end 20 of the pre-loaded tip 16 (as will be described herein). While the illustrated embodiment provides a generally frusto-conical or funnel-shaped distal portion 36 with a smoothly tapered diameter, it is within the scope of the present disclosure for the alignment member 28 to be differently configured.

Figure 5:
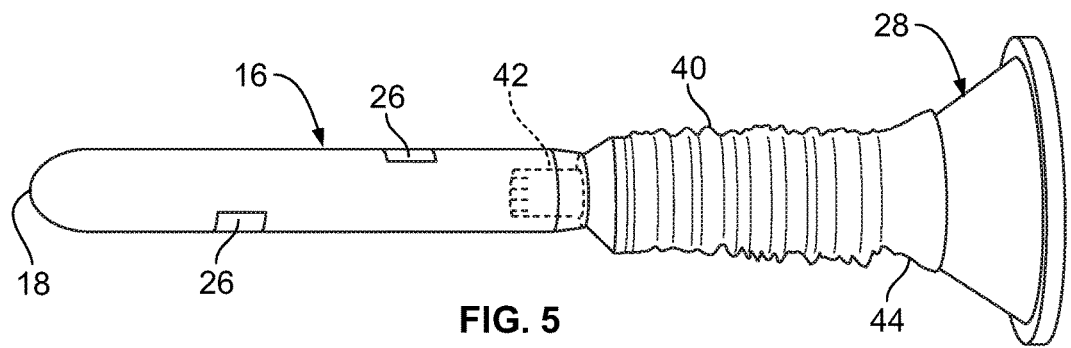
FIG. 5 is a side elevational view of the pre-loaded tip and funnel of FIG. 4, with a portion of the alignment member positioned within a protective sleeve.
Figure 17:
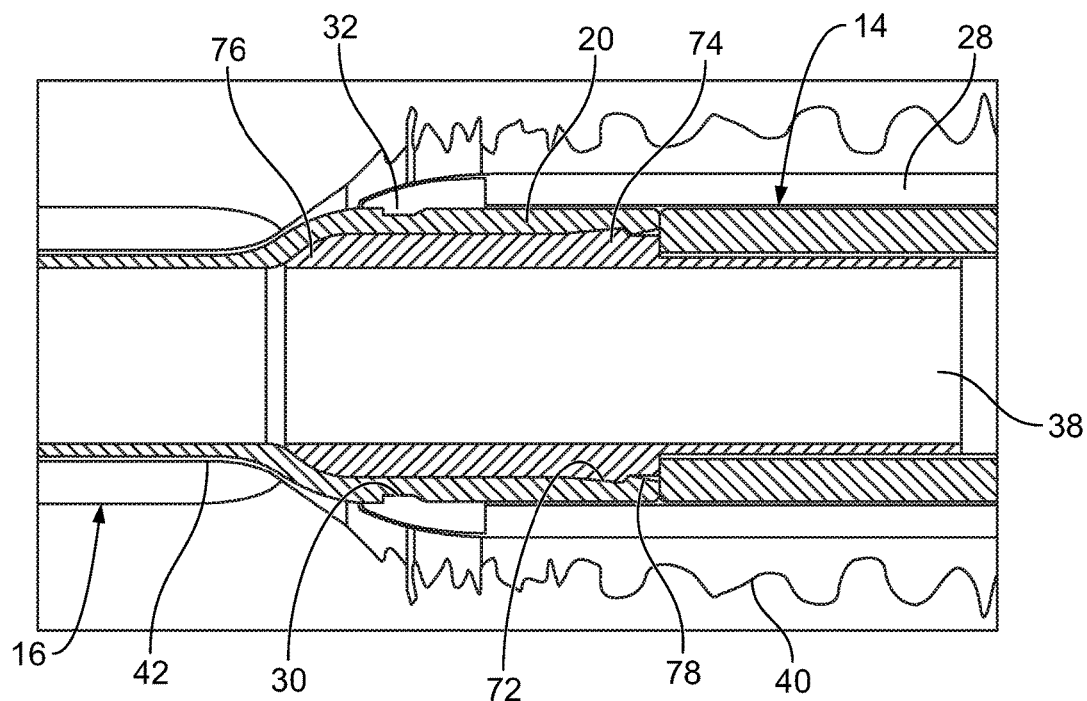
FIG. 17 is a cross-sectional view of the catheter member in engagement with the pre-loaded tip.

FIG. 5 shows the pre-loaded tip 16 and alignment member 28 with a generally tubular protective sleeve 40 surrounding at least the proximal portion 34 of the alignment member 28. FIG. 17 also shows the arrangement of the sleeve 40 with respect to the pre-loaded tip 16 and the alignment member 28. In the illustrated embodiment, the distal end 20 of the pre-loaded tip 16 is separately formed from the proximal portion 24, in which case the distal end 20 of the pre-loaded tip 16 may be inserted into the protective sleeve 40 prior to the distal end 20 being secured to the proximal portion 24 of the pre-loaded tip 16. By such a configuration, the proximal end 42 of the protective sleeve 40 is sandwiched between the outer surface of the distal end 20 of the pre-loaded tip 16 and the inner surface of the proximal portion 24 of the pre-loaded tip 16, thereby securing the proximal end 42 of the protective sleeve 40 to the pre-loaded tip 16. In other configurations, the proximal end 42 of the protective sleeve 40 may be secured to the pre-loaded tip 16 by other means, such as using an adhesive or a heat seal the like.

Regardless of how the proximal end 42 of the protective sleeve 40 is secured to the pre-loaded tip 16, the distal end 44 may be secured to the alignment member 28, as shown in FIG. 5, using any suitable means (e.g., an adhesive or a heat seal or a fastener or the like). Preferably, the protective sleeve 40 is elongated, having a length that is greater than the distance between its proximal and distal ends 42 and 44 in the configuration of FIG. 5, in which case the protective sleeve 40 may be mounted on the alignment member 28 in a bunched or folded arrangement. When the pre-loaded tip 16 is separated from the alignment member 28, as will be described in greater detail herein, the protective sleeve 40 becomes unbunched or unfolded to allow the distance between the proximal and distal ends 42 and 44 of the protective sleeve 40 to increase, up to the completely unbunched or unfolded length of the protective sleeve 40.

As will be described herein, the protective sleeve 40 covers the catheter member 14 as it is advanced into and through a body lumen, thereby providing a barrier which prevents bacteria on the catheter member 14 from contacting the body lumen. Additionally, the protective sleeve 40 may provide lubricity to aid catheter insertion. The protective sleeve 40 may be an inherently lubricious film or may have a lubricious coating applied thereto, as will be described herein. By providing a protective sleeve 40 which covers the catheter member 14 as it is advanced out of the cartridge 12, the catheter member 14 may be uncoated or otherwise omit a lubricious coating and may be directly handled by a user without the risk of bacteria being transferred to the catheter member 14 and then from the catheter member 14 to the aforementioned body lumen.

FIG. 6 shows the proximal end 18 of the pre-loaded tip 16 positioned within an introducer 46. The introducer 46 extends between a distal end, which may include a flange or collar 48, and a proximal end 50. The introducer 46 (except for the flange 48, if provided) may be configured for insertion into a body lumen (e.g., a urethral opening) prior to advancement of the pre-loaded tip 16 and catheter member 14 into the body lumen (which will be described herein), in which case it may be advantageous for the introducer 46 (except for the flange 48, if provided) to be formed of a soft, transparent material for improved comfort and visibility.

Figure 18:
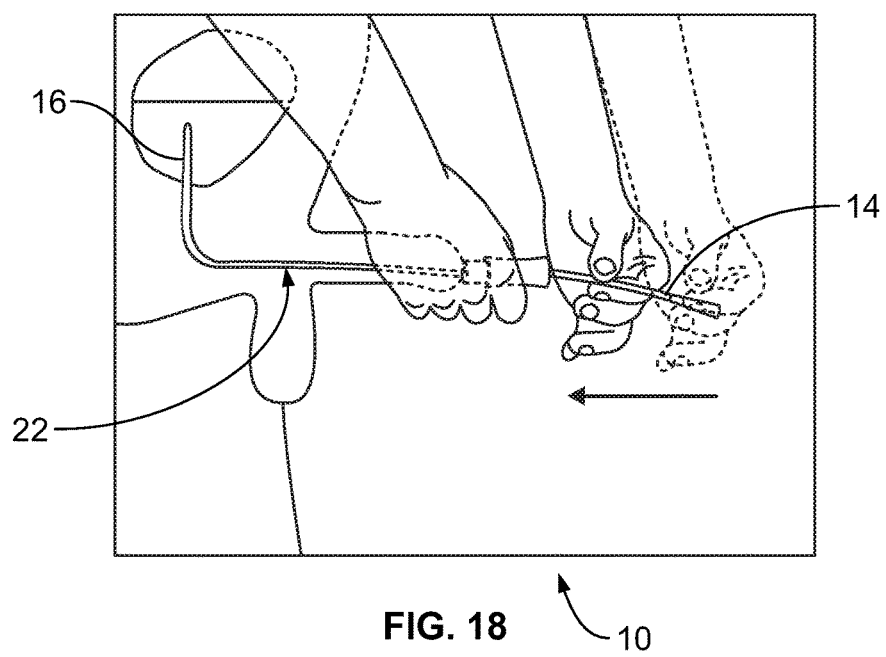
FIG. 18 illustrates another step of an exemplary method of using a catheter cartridge assembly according to the present disclosure, in which the pre-loaded tip and catheter member are advanced proximally into the urethra.
Figure 19:
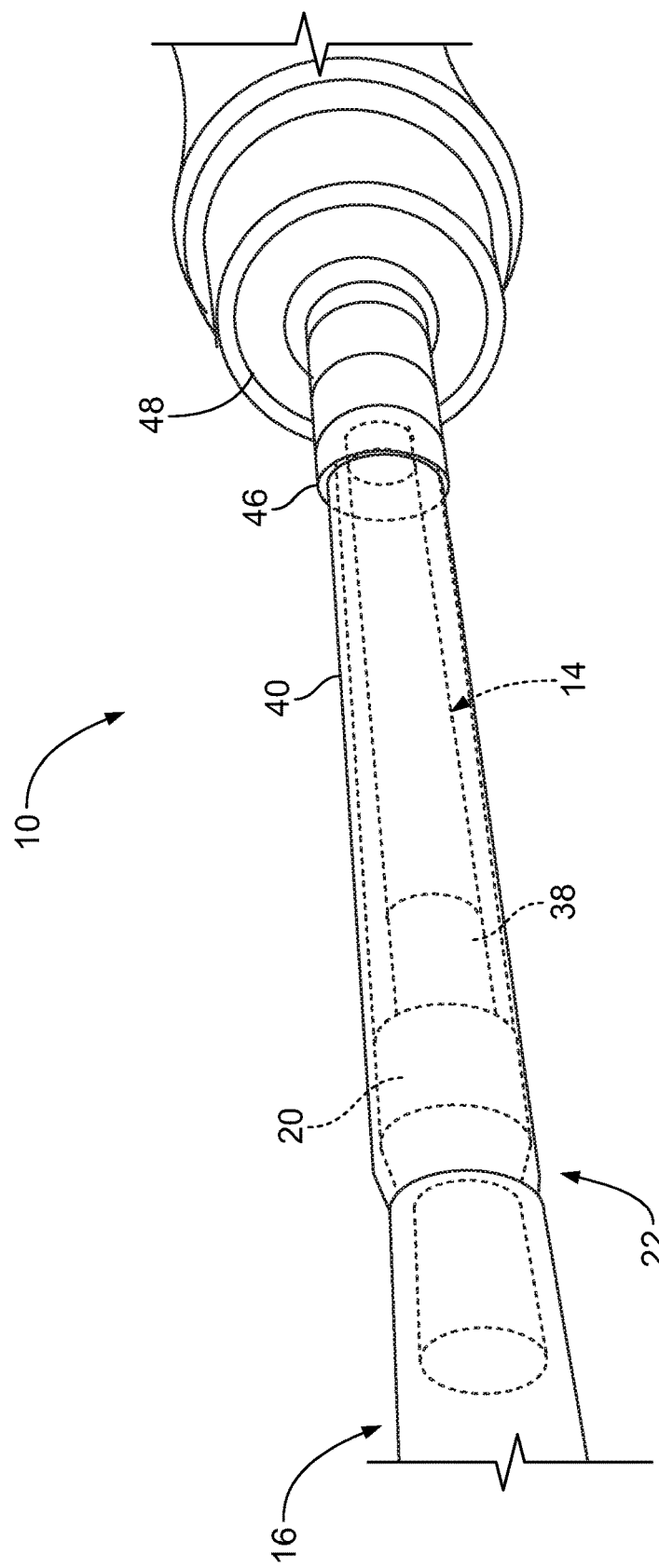
FIG. 19 is a perspective view of the pre-loaded tip and catheter member partially advanced out of the cartridge, with a portion of the pre-loaded tip and catheter member positioned within the protective sleeve.

The proximal end 50 of the introducer 46 may include an aperture or opening that may be moved between a closed configuration (in which there is no object positioned within the opening, as in FIG. 6) and an open configuration (in which the pre-loaded tip 16 or catheter member 14 or any other object is partially positioned within or extending through the opening, with a portion of the object positioned within the introducer 46 and another portion positioned outside of the introducer 46, as in FIGS. 18 and 19). In one embodiment, the proximal opening may be provided as a slit opening with one or more slits or cuts defining a plurality of deformable petals that may be moved to define the aforementioned open and closed configurations. In other embodiments, the opening may be differently configured, provided that it is configured to allow passage of the pre-loaded tip 16 or the catheter member 14 therethrough.

FIG. 7 illustrates portions of the pre-loaded tip 16, alignment member 28, and protective sleeve 40 positioned within a reservoir 52, which may be a lubrication reservoir. In the illustrated embodiment, the lubrication reservoir 52 is generally tubular or frusto-conical, with a proximal end 54 of the lubrication reservoir 52 secured to the flange 48 of the introducer 46 and a distal end 56 of the lubrication reservoir 52 secured to the alignment member 28. The lubrication reservoir 52 may contain a fluid, in which case it may be preferred for the proximal and distal ends 54 and 56 of the lubrication reservoir 52 to form fluid-tight seals with the introducer flange 48 and the alignment member 28, respectively. In particular, the lubrication reservoir 52 may contain a wetting agent or lubricating fluid to contact the protective sleeve 40 within the lubrication reservoir 52. For example, the lubrication reservoir 52 may contain a lubricating gel that contacts and lubricates the outer surface of the protective sleeve 40. In an alternative embodiment, the lubrication reservoir 52 may include a wetting agent, such as water, when the protective sleeve 40 is formed of a material (e.g., a hydrophilic polymer) that becomes lubricious when wetted with a wetting agent.

FIG. 8 illustrates the lubrication reservoir 52 and protective sleeve 40, along with portions of the pre-loaded tip 16 and the alignment member 28, positioned within a cartridge housing 58. In the illustrated embodiment, the cartridge housing 58 is generally tubular, with a proximal portion 60 secured to the introducer flange 48 and a distal portion 62 secured to a distal end of the alignment member 28. A portion of the introducer 46 may remain outside of the cartridge housing 58, as shown in FIG. 8. The cartridge housing 58 is the portion of the cartridge 12 that is directly handled during use of the catheter cartridge assembly 10, so it may be contoured and/or include various ergonomic features for improved handling.

The cartridge 12 may further include a proximal enclosure 64 associated with the proximal portion 60 of the cartridge housing 58 and a distal enclosure 66 associated with the distal portion 62 of the cartridge housing 58, as shown in FIG. 9. In the illustrated embodiment, the proximal enclosure 64 is provided as a twist-off cap to work in combination with external threads 68 of the proximal portion 60 of the cartridge housing 58 to selectively cover and uncover the introducer 46, but may be otherwise configured. In the illustrated embodiment, the distal enclosure 66 is provided as a ring-pull (e.g., a foil or nylon film or the like) which is detachably sealed or secured to the distal portion or end 62 of the cartridge housing 58, but may be otherwise configured. While the illustrated proximal enclosure 64 is configured to be reconnected to the cartridge housing 58 and the illustrated distal enclosure 66 is configured to be permanently detached from the cartridge housing 58, it is within the scope of the present disclosure for either or both of the enclosures to be reconnectable to the cartridge housing 58 after being initially removed or for either or both of the enclosures to be permanently detached from the cartridge housing 58. For example, either or both of the enclosures may be provided as a reattachable cap or a ring-pull or a frangible cover or the like. Additionally, either or both of the enclosures may be provided with grip features or contours for improved handling.

As for the catheter member 14 of FIG. 2, it may be a generally tubular device which is flexible, but with sufficient column strength to be advanced through a body lumen without collapsing. In the illustrated embodiment, the catheter member 14 includes a tubular midsection 68, with a drainage device 70 positioned at the distal end of the midsection 68 and a fitting or connector or proximal end 38 at the opposite end of the midsection 68. In one embodiment, the tubular midsection 68 may be formed of a softer material than a typical catheter and may be directly handled by a user, in which case the catheter member 14 may be more easily and compactly stored and transported for daily use, such as in the pocket of the user. Furthermore, if the catheter member 14 is provided as a reusable device, a user is free to carry only a single catheter member 14 for use throughout the day, rather than carrying multiple catheters. The cartridge 12 itself may be relatively compact compared to typical catheters, with the cartridge 12 being approximately 75 mm long and 20 mm wide in one embodiment in which the catheter cartridge assembly 10 is used for intermittent catheterization of a male urethra, whereas a typical male urinary catheter may be approximately 400 mm long.

If the catheter member 14 is configured as a reusable device, it may be advantageous for all or a portion of its internal surface to include a coating to prevent wetting and/or inhibit bacterial growth therein. In one embodiment, all or a portion of the internal surface of the catheter member 14 may be provided with a hydrophobic coating, although it is within the scope of the present disclosure for all or a portion of the internal surface of the catheter member 14 to include a different coating. No external coating is required for the catheter member 14, because the protective sleeve 40 covers the portion of the catheter member 14 positioned within a body lumen during use. As such, any portion of the catheter member 14 may be handled during use, which makes for improved handling by a user in contrast to known catheter devices, wherein only a portion of the catheter (e.g., the drainage device at the distal end) may be handled during use.

The drainage device 70 of the catheter member 14 may be omitted, depending on the intended use of the catheter cartridge assembly 10, but may be advantageously included if the catheter cartridge assembly 10 is intended to drain a body fluid from a body lumen, such as draining urine from a bladder and urethra. In the illustrated embodiment, the drainage device 70 has a generally funnel-shaped configuration (similar to the shape of the alignment member 28), but it may be variously configured, provided that it is suitable for draining a fluid from the catheter member 14 into a disposal location or receptacle (e.g., a toilet).

The proximal end 38 of the catheter member 14 provides a counterpart to the distal end 20 of the pre-loaded tip 16 of the cartridge 12. The proximal end 38 of the catheter member 14 is shown in greater detail in FIG. 17, which illustrates the proximal end 38 of the catheter member 14 engaged with the distal end 20 of the pre-loaded tip 16. In the illustrated embodiment, the internal surface of the distal end 20 of the pre-loaded tip 16 includes a groove or formation 72 which receives a projection or ridge 74 of the proximal end 38 of the catheter member 14 to connect the pre-loaded tip 16 and the catheter member 14 as a composite catheter 22 when the catheter member 14 is proximally advanced into contact with the pre-loaded tip 16. The illustrated arrangement provides a snap-fit between the pre-loaded tip 16 and the catheter member 14, which allows the pre-loaded tip 16 to be selectively attached and detached from the catheter member 14. While the illustrated embodiment provides a snap-fit between the pre-loaded tip 16 and the catheter member 14, other arrangements (e.g., a friction fit or press fit or interference fit or the like) may also be provided for detachably connecting the pre-loaded tip 16 and the catheter member 14. The proximal end 38 of the catheter member 14 may include a tapered lead-in portion 76 (FIG. 17), with the distal end 20 of the pre-loaded tip 16 also including a tapered lead-in portion 78 to facilitate proximal relative movement of the catheter member 14 with respect to the pre-loaded tip 16 to connect the two components together.

Figure 10:
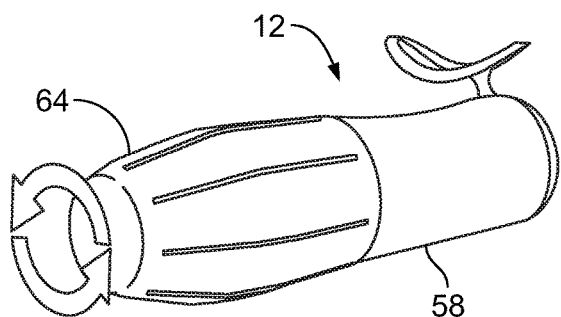
FIG. 10 illustrates a step of an exemplary method of using a catheter cartridge assembly according to the present disclosure, in which the proximal enclosure is removed from the cartridge.
Figure 11:
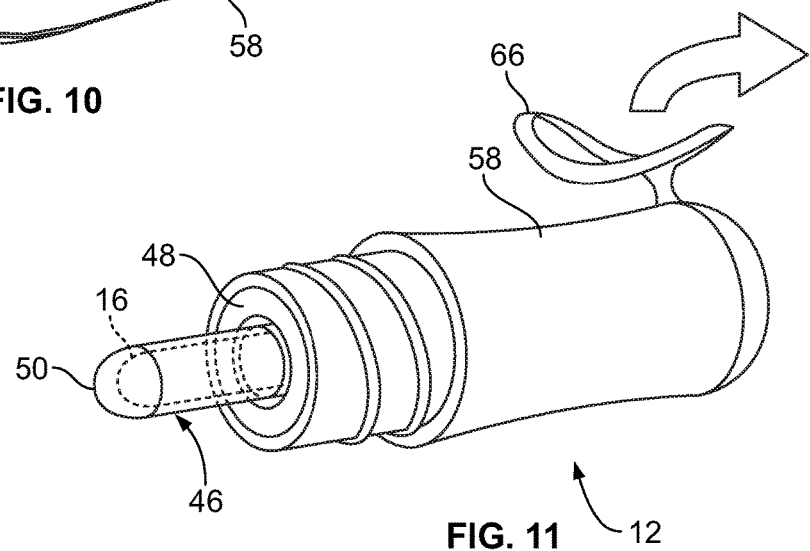
FIG. 11 illustrates another step of an exemplary method of using a catheter cartridge assembly according to the present disclosure, in which the distal enclosure is removed from the cartridge.

In an exemplary method, a catheter cartridge assembly 10 may be used for intermittent catheterization of a male urethra. In this exemplary method, a user removes the proximal and distal enclosures 64 and 66 from the cartridge housing 58 (FIGS. 10 and 11). Preferably, the enclosures 64 and 66 are configured to be relatively quiet when removed from the cartridge housing 58 compared to typical foil packages of existing catheter devices. If an enclosure is configured to be reattached to the cartridge housing 58 following use, the enclosure may be retained by the user, otherwise the enclosures may be discarded.

Figure 12:
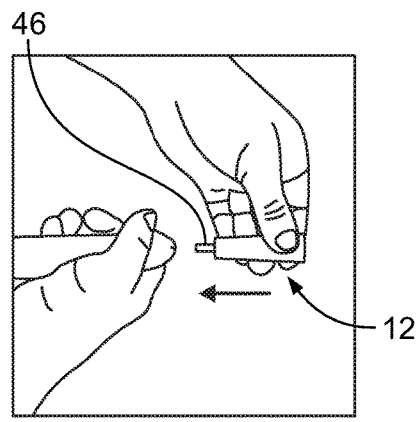
FIGS. 12 and 13 illustrate another step of an exemplary method of using a catheter cartridge assembly according to the present disclosure, in which the introducer is advanced into a urethra.
Figure 13:
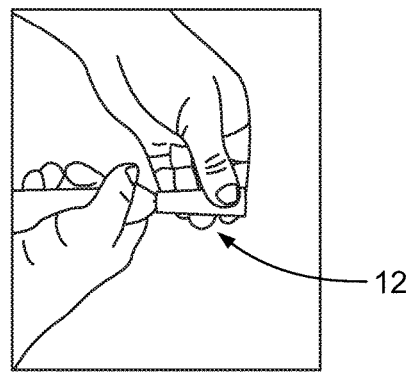

With the enclosures 64 and 66 removed from the cartridge housing 58, the introducer 46 may be proximally advanced into the urethra until the introducer flange 48 or cartridge housing 58 contacts the penis, as in FIGS. 12 and 13.

Figure 14:
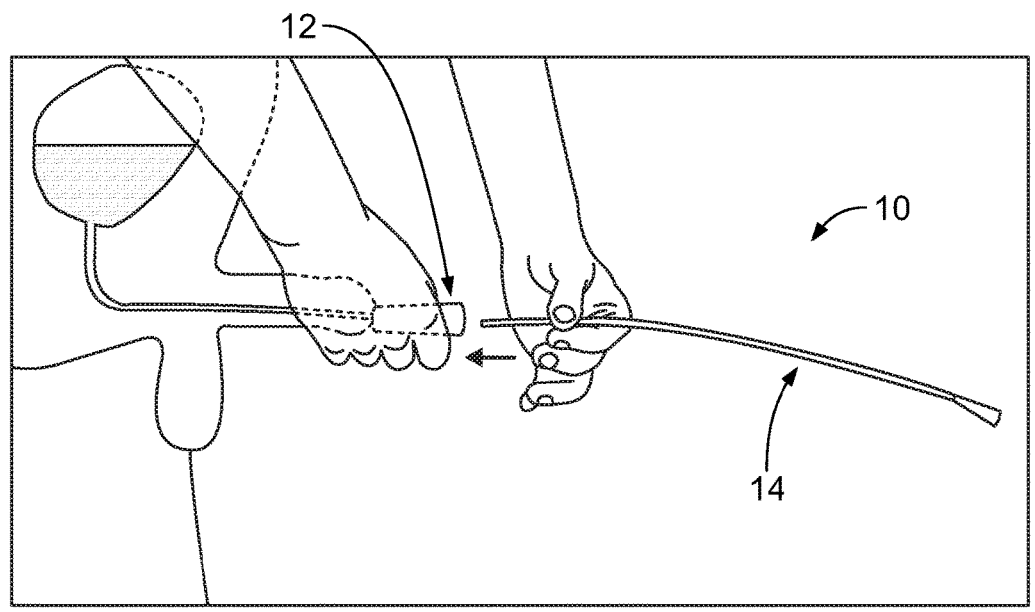
FIG. 14 illustrates another step of an exemplary method of using a catheter cartridge assembly according to the present disclosure, in which the catheter member is advanced proximally into the cartridge.
Figure 15:
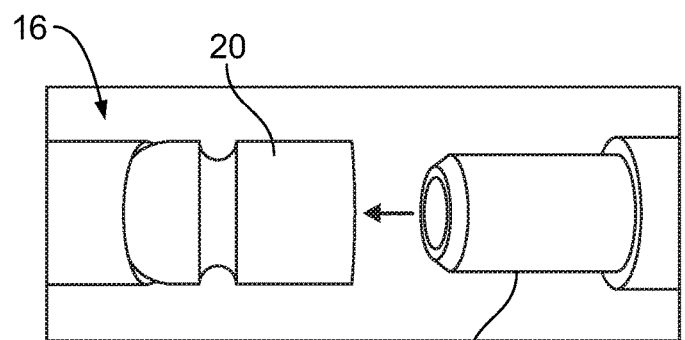
FIGS. 15 and 16 illustrate a proximal end of the catheter member moving into engagement with a distal end of the pre-loaded tip.
Figure 16:
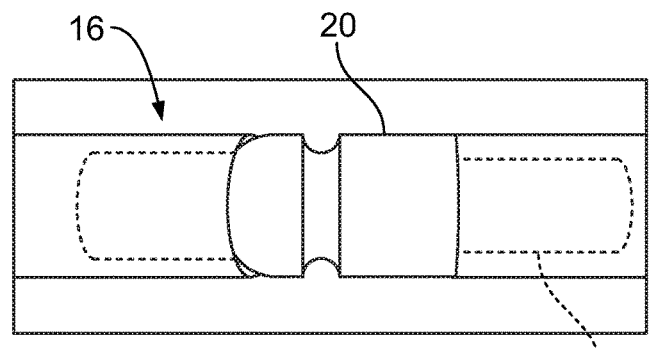

Next, the user holds the cartridge 12 in place while proximally advancing the catheter member 14 toward and into the cartridge 12, as in FIG. 14. As shown in FIG. 14, the user may grip any portion of the catheter member 14 (including the tubular midsection 68) during use, which makes it easier for the user to properly advance the proximal end 38 of the catheter member 14 into the cartridge 12 via the distal end 62 of the cartridge housing 58. If the proximal end 38 of the catheter member 14 is not aligned with the distal end 20 of the pre-loaded tip 16, the proximal end 38 of the catheter member 14 contacts the alignment member 28 and is moved into alignment with the distal end 20 of the pre-loaded tip 16. Continued proximal advancement of the catheter member 14 causes the proximal end 38 of the catheter member 14 to engage and become detachably connected to the distal end 20 of the pre-loaded tip 16, as shown in FIGS. 15-17.

The joined pre-loaded tip 16 and catheter member 14 may thereafter be proximally advanced together as a composite catheter 22 (FIG. 18). The composite catheter 22 exits the introducer 46 and enters the urethra. As the composite catheter 22 exits the introducer 46, the protective sleeve 40 unfurls to cover the catheter member portion 14 of the composite catheter 22, as shown in FIG. 19. The pre-loaded tip portion 16 of the composite catheter 22 does not need to be covered by the protective sleeve 40 because it remains in a sterile condition within the cartridge housing 58 prior to use, and is advanced directly into the urethra during use.

Figure 20:
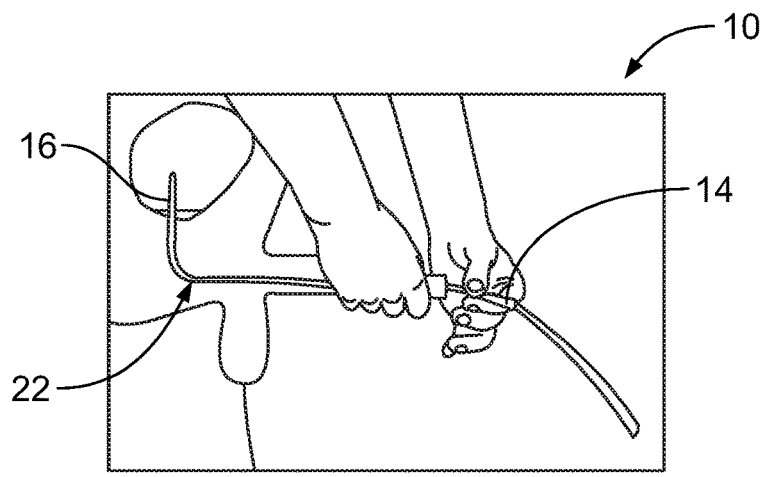
FIG. 20 illustrates another step of an exemplary method of using a catheter cartridge assembly according to the present disclosure, in which urine is drained from the bladder using the catheter cartridge assembly.

The composite catheter 22 is proximally advanced through the urethra until the pre-loaded tip portion 16 enters the bladder (FIG. 18). With the pre-loaded tip portion 16 in the bladder, urine drains from the bladder into the composite catheter 22 via the eyes 26 of the pre-loaded tip portion 16. The urine flows through the composite catheter 22 from the pre-loaded tip portion 16 to the catheter member portion 14, until it flows out of the catheter member portion 14 via the drainage device 70 (FIG. 20). The urine may be directed into a toilet or other disposal location or receptacle.

Figure 21:
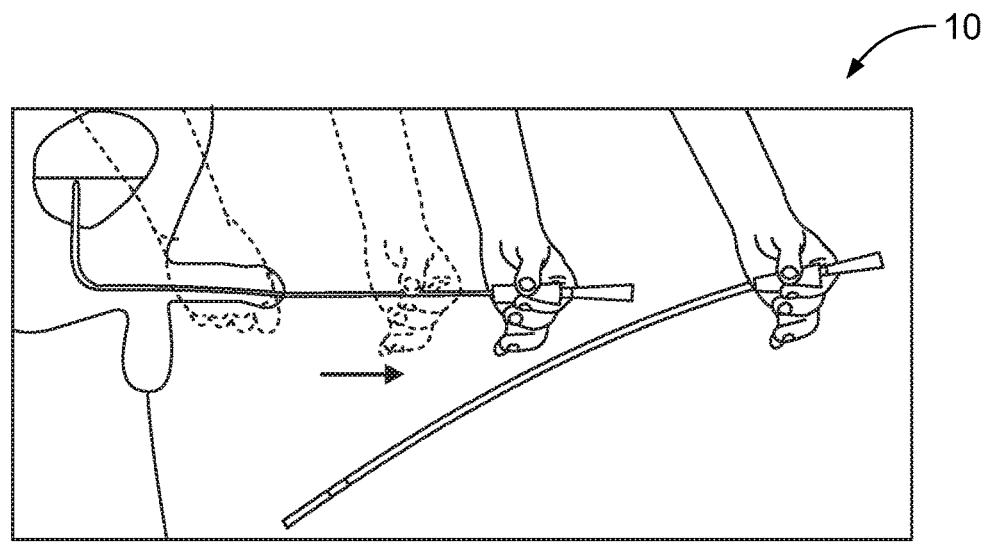
FIG. 21 illustrates another step of an exemplary method of using a catheter cartridge assembly according to the present disclosure, in which the catheter cartridge assembly is withdrawn from the urethra.

When the bladder has been suitably emptied, the composite catheter 22 and introducer 46 may be removed from the urethra (FIG. 21). This may be done in any of a variety of ways, such as by simultaneously gripping the cartridge housing 58 and catheter member portion 14 of the composite catheter 22 and moving them distally or sliding the cartridge housing 58 distally along the catheter member portion 14 of the composite catheter 22 to engage the drainage device 70, with further distal movement of the cartridge housing 58 serving to withdraw the composite catheter 22 from the urethra.

Figure 22:
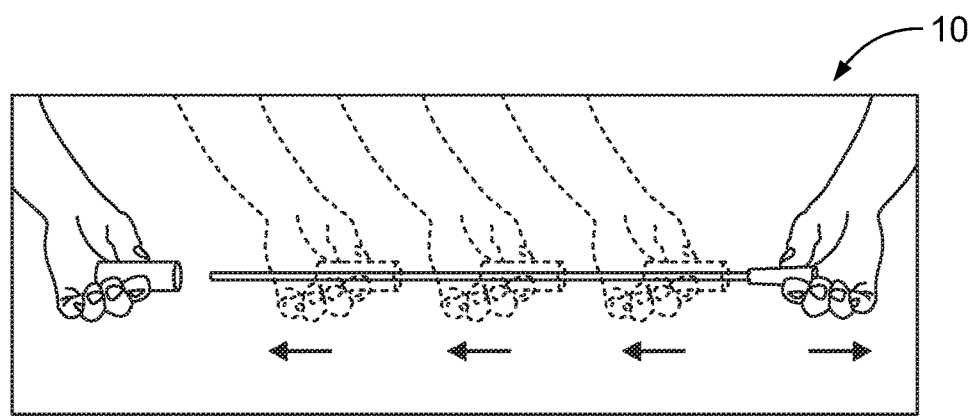
FIG. 22 illustrates another step of an exemplary method of using a catheter cartridge assembly according to the present disclosure, in which the catheter member is detached from the cartridge.
Figure 23:
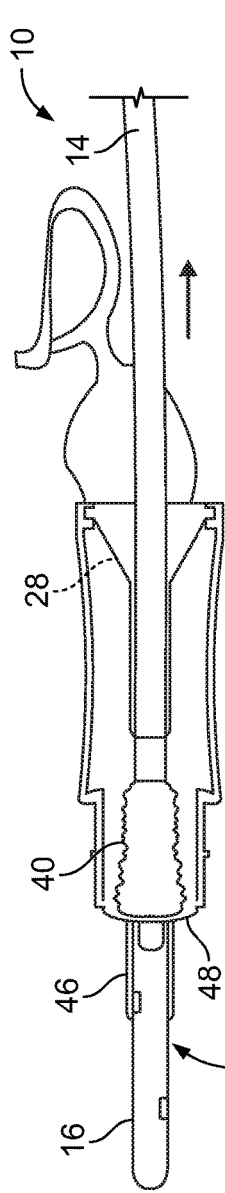
FIGS. 23-25 illustrate the catheter member being detached from the cartridge, as in FIG. 22.
Figure 24:
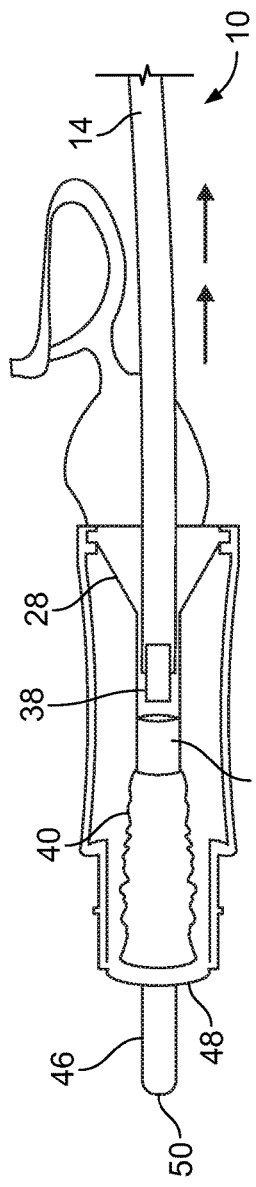
Figure 25:
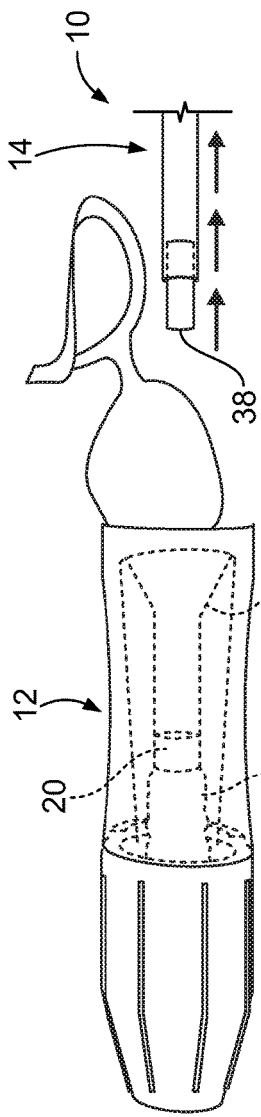

After use, the catheter cartridge assembly 10 may be disassembled by detaching the catheter member 14 from the cartridge 12 (FIG. 22). This may be achieved by gripping the cartridge housing 58 and then moving the composite catheter 22 distally with respect to the cartridge housing 58 (FIG. 23). Upon sufficient relative movement of the cartridge 12 and the composite catheter 22, the pre-loaded tip 16 comes into contact with the alignment member 28. Further relative movement presses the pre-loaded tip 16 against the alignment member 28 until the proximal end 38 of the catheter member 14 detaches from the distal end 20 of the pre-loaded tip 16 (FIG. 24). Thereafter, the catheter member 14 may be backed out of the cartridge 12 to fully dissociate it from the cartridge 12 (FIG. 25).

With the catheter member 14 separated from the cartridge 12, the cartridge 12 may be discarded. If the cartridge 12 cannot be immediately discarded, the user may reattach one or both of the enclosures to the cartridge housing 58 for improved storage and transport until it can be discarded. As for the catheter member 14, it may be retained for further use (optionally after being washed, rinsed, or re-sterilized) with a new cartridge 12.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A catheter cartridge assembly, comprising:
a cartridge including
a cartridge housing having proximal and distal ends;
a pre-loaded tip at least partially positioned within the cartridge housing; and
a protective sleeve at least partially positioned within the cartridge housing and having a proximal end secured with respect to the pre-loaded tip; and
a catheter member having a proximal end configured to be advanced proximally into and through the cartridge housing to engage and become joined to a distal end of the pre-loaded tip for proximal advancement out of the proximal end of the cartridge housing as a composite catheter defined by the joined pre-loaded tip and catheter member, wherein the protective sleeve is configured to cover the portion of the composite catheter defined by the catheter member as the composite catheter is proximally advanced out of the cartridge housing.

2. The catheter cartridge assembly of claim 1, further comprising an alignment member at least partially positioned within the cartridge housing and configured to guide the proximal end of the catheter member into engagement with the distal end of the pre-loaded tip as the catheter member is advanced proximally through the cartridge housing.

3. The catheter cartridge assembly of claim 2, wherein the alignment member is detachably connected to the pre-loaded tip via a snap-fit.

4. The catheter cartridge assembly of claim 2, wherein the alignment member is detachably connected to the pre-loaded tip via a friction fit.

5. The catheter cartridge assembly of claim 1, further comprising a reservoir at least partially positioned within the cartridge, with at least a portion of the pre-loaded tip and at least a portion of the protective sleeve positioned within the reservoir.

6. The catheter cartridge assembly of claim 1, further comprising an introducer connected to the proximal end of the cartridge housing, with at least a portion of the pre-loaded tip positioned within the introducer.

7. The catheter cartridge assembly of claim 1, further comprising a proximal enclosure associated with a proximal portion of the cartridge housing and a distal enclosure associated with a distal portion of the cartridge housing.

8. The catheter cartridge assembly of claim 1, wherein the catheter member includes an internal coating.

9. The catheter cartridge assembly of claim 1, wherein the proximal end of the catheter member and the distal end of the pre-loaded tip are configured to engage and become joined as a snap-fit.

10. The catheter cartridge assembly of claim 1, wherein the proximal end of the catheter member and the distal end of the pre-loaded tip are configured to engage and become joined as a friction fit.

11. A catheterization method employing a cartridge including a cartridge housing having proximal and distal ends, a pre-loaded tip at least partially positioned within the cartridge housing, and a protective sleeve having a proximal end secured with respect to the pre-loaded tip, the method comprising:
proximally advancing at least a proximal portion of a catheter member into the cartridge housing via the distal end of the cartridge housing;
engaging a proximal end of the catheter member and a distal end of the pre-loaded tip, thereby joining the catheter member and the pre-loaded tip so as to define a composite catheter; and
advancing said composite catheter out of the cartridge housing via the proximal end of the cartridge housing, with the protective sleeve covering the portion of the composite catheter defined by the catheter member as the composite catheter is advanced out of the cartridge housing.

12. The catheterization method of claim 11, wherein
the cartridge includes an alignment member at least partially positioned within the cartridge housing, and
the alignment member is configured to guide the proximal end of the catheter member into engagement with the distal end of the pre-loaded tip.

13. The catheterization method of claim 12, wherein said advancing said composite catheter out of the cartridge housing via the proximal end of the cartridge housing includes first detaching the pre-loaded tip from the alignment member.

14. The catheterization method of claim 11, wherein
the cartridge includes a proximal enclosure removably connected to a proximal portion of the cartridge housing, and
said advancing said composite catheter out of the cartridge housing via the proximal end of the cartridge housing includes first at least partially disassociating the proximal enclosure from the proximal portion of the cartridge housing.

15. The catheterization method of claim 11, wherein
the cartridge includes a distal enclosure removably connected to a distal portion of the cartridge housing, and
said proximally advancing at least a proximal portion of a catheter member into the cartridge housing via the distal end of the cartridge housing includes first at least partially disassociating the distal enclosure from the distal portion of the cartridge housing.

16. The catheterization method of claim 11, wherein said engaging a proximal end of the catheter member and a distal end of the pre-loaded tip includes engaging and joining the proximal end of the catheter member and the distal end of the pre-loaded tip with a snap-fit.

17. The catheterization method of claim 11, wherein said engaging a proximal end of the catheter member and a distal end of the pre-loaded tip includes engaging and joining the proximal end of the catheter member and the distal end of the pre-loaded tip with a friction fit.

18. The catheterization method of claim 11, further comprising retracting the composite catheter distally into the cartridge housing; and detaching the catheter member from the pre-loaded tip.

19. The catheterization method of claim 11, further comprising disposing of the cartridge after catheterization, while retaining the catheter member for reuse.

\* \* \* \* \*